(12) United States Patent
Morenkova

(10) Patent No.: US 6,770,276 B1
(45) Date of Patent: Aug. 3, 2004

(54) INSULIN-CONTAINING MEDICAMENT FOR PERORAL APPLICATION AND METHOD FOR THE PRODUCTION THEREOF

(75) Inventor: Svetlana Alexandrovna Morenkova, Moscow (RU)

(73) Assignee: Otkrytoe Aktsionernoe Obschestvo "Quantum Satis", Moscow (RU)

(*) Notice: Subject to any disclaimer, the term of this patent is extended or adjusted under 35 U.S.C. 154(b) by 0 days.

(21) Appl. No.: 09/890,353

(22) PCT Filed: Dec. 1, 1999

(86) PCT No.: PCT/RU99/00463

§ 371 (c)(1),
(2), (4) Date: Jul. 30, 2001

(87) PCT Pub. No.: WO01/39794

PCT Pub. Date: Jun. 7, 2001

(30) Foreign Application Priority Data

Nov. 30, 1999 (RU) .......................................... 99124800

(51) Int. Cl.[7] .......................... A01N 63/00; A01N 65/00
(52) U.S. Cl. .................. 424/93.73; 424/93.7; 424/93.1
(58) Field of Search .......................... 424/93.73, 93.7, 424/93.1

(56) References Cited

U.S. PATENT DOCUMENTS

| 5,438,040 A | 8/1995 | Ekwuribe ........................ 514/3 |
| 5,665,700 A | * 9/1997 | Cho et al. |
| 5,698,515 A | 12/1997 | Plate et al. ..................... 514/3 |

FOREIGN PATENT DOCUMENTS

| EP | 0127535 B1 | 1/1990 |
| RU | 2058788 | 4/1996 |
| RU | 2066551 | 9/1996 |
| RU | 2117488 | 8/1998 |
| WO | WO96/31231 | 10/1996 |
| WO | WO96/37215 | 11/1996 |
| WO | WO99/40932 | 8/1999 |

OTHER PUBLICATIONS

Publication No. 1997-041104, date Apr. 1996, inventor Morenkova, Derwent publication.*
Ziv et al, J Pharm Sci 83 (6), "Oral administration of insulin in solid form to nondiabetic . . . ", Jun. 1994, pp. 792–794.
Cho et al. Lancet, "Oral Delivery of Insulin", Dec. 23/30, 1989, pp. 1518–1519.
Safran et al, Science, vol. 233, "A New Approach to the Oral Administration of Insulin . . . ", 1986, pp. 1081–1083.

* cited by examiner

*Primary Examiner*—Chris Tate
*Assistant Examiner*—Randall Winston
(74) *Attorney, Agent, or Firm*—Jacobson Holman PLLC

(57) ABSTRACT

The invention refers to medical science and deals with insulin-containing medicine for peroral use and its derivation method.

Insulin-containing medicine for peroral use containing insulin and auxiliary substance, wherein it contains insulin immobilized on erythrocytes of fresh mammal blood in the presence of stitching agent in proportion, in mass %:

| insulin | 5–10 |
| erythrocytes execreted from fresh mammal blood | 100 | and represents a lyophilized form with the content 1250–2000E of insulin on 1 g of dry mass.

13 Claims, No Drawings

INSULIN-CONTAINING MEDICAMENT FOR PERORAL APPLICATION AND METHOD FOR THE PRODUCTION THEREOF

The invention refers to medical science and deals with insulin-containing medicine for peroral use and its derivation method.

PRECEDING LEVEL OF TECHNIQUE

Diabetes—is one of the most widespread severe diseases, the absolute or relative deficiency of pancreas hormone, insulin, of which underlies it.

Insulin is a half-peptide hormone with molecular mass 6000. It impacts all types of metabolism in any organism: increases the penetration of glucose into organism tissues, prompts its utilization, reduces content of glycogen in liver and increases its number in muscles, enhances the intensity of protein synthesis and slows decomposition of the latter.

The principal method for injection of insulin into a human organism is hypodermic and intramuscular injection of medication. The attempts of insulin injection in the most physiological and patient-suitable peroral way turned out to be unsuccessful, for insulin easily degrades under the influence of digestive ferments, the fact that leads to loss of its biological activity.

The main obstacle, occurred when creating peroral forms of insulin, is its low resistance to the behavior of proteolitic ferments of gastrointestinal tract Over the last decade there were numerous attempts to create peroral forms of insulin, nevertheless, so far it was impossible to create the efficiently acting medicine, able to compete in terms of its active properties with insulin injected The medicine of insulin for peroral use, which represents a water-oily micro-emulsion consisting of insulin, lipids and protease deterrent, is well known Micro-emulsion is then covered with carboxymethylcellulos (Cho Y. W., Flynn M., Lancet, 1989, #30, p. 1518 Saffran , Kurnar G. S.).

The substantial deficiency of this medicine along with the labor-intensive and expensive technology of manufacturing is the carrier—carboxymethylcellulos which is subject to influence of micro-organism as well as able to absorb a great number of insulin, as the result of which the form derived doesn't correspond with the requirements of the efficient peroral use of insulin.

There is a widespread notion about insulin-containing medicine consisting of the core with the content of insulin and auxiliary substances and capsule made of biodegrading medium polymer (Savarlar C., et al, A new approach to the oral administration of insulin and other peptide drugs, Science, 1986, v.233, pp.1081–1084).

The medicine is produced by injection of 1–40 mg of crystal insulin and 200 mg of stoichiometric impurity of 5-methoxisalicylic acid and sodium bicarbonate. Then the capsule (tablet) is covered with so-polymer of hydroxiethylmethacrylate and styrene, stitched with devinylazobenzene. The capsule is resistant to the effect of stomach medium and thin intestines, but gets decomposed in thick intestines under the influence of microorganisms existing there.

The deficiency of this medium is its low efficiency and undefined time for reaching maximum effect. Peroral injection of the said medicine, containing 1 unit of insulin, into rats leads to reduction of glucose concentration in blood by 20% within 9 hours after the injection At the same time the intramuscular injection of insulin solution in the dose 0,1 or 1,0 units causes the reduction in the level of glucose in blood by 39 and 63% respectively. The maximum hypoglycemic effect for certain animals is reached within the period from 1 to 9 hours, and for some animals the effect of reduction in glucose concentration is missing even in 10 hours after the injection of medicine.

A solid insulin-containing medicine, consisting of the core containing inhibitor of proteolitic ferments and auxiliary substances and stomach-resistant capsule (Ehud Ziv, Miriarn Kidron, Itanaar Raz et al., Oral administration of insulin of solid form to non-diabetic and diabetic dogs. Journal of Pharmaceutical Science 1994, x.83,#6, pp.792–794 and Kidron A, Krausz M., Raz I et al., The absorption of Insulin: from the intestine in dogs, Nenside. Surfactants. Deterg 1989, v.26, #5, pp.352–354) is well known.

The medicine contains the inhibitor of trypsin made of soy as the inhibitor of proteolitic ferments and sodium cholate and lactose—as auxiliary substances. Lactose is used as a non-active filler, and sodium cholate as a compound enabling to enhance the penetration of insulin through intestine walls.

The deficiency of this medicine is its low efficiency. Thus, when the medicine is injected in a peroral way into healthy dogs with the insulin dose 40 units/kg. of animal's weight, the maximum reduction in glucose concentration in animal's blood makes 18%, though with a hypodermic injection the similar hypoglycemic effect may be reached with the insulin dose 10 times lower. Besides, the abovementioned medicine containing the inhibitor of trypsin made of soy has a selective effect towards various types of animals, in other words, it is not a universal one. Thus, when used in a perotal way it reveals activity towards dogs and reveals no activity towards rats (Kidron A, Krausz M., Raz I et al., The absorption of Insulin: from the intestine in dogs, Nenside. Surfactants. Deterg. 1989, v.26, #5, pp.352–354).

An insulin-containing medicine, intended to treat patients with diabetes in a peroral way, which consists of the core sampling containing insulin, albuminous inhibitor of proteolitic ferments , and represents a stitched hydrophilic polymer, modified by ovomukoide, and auxiliary substances and stomach-resistant capsule (Ru Nr.2117488 Cl, 20.08.98) is well known.

The medicine contains 10 UNITS of insulin per one tablet. The medicine ensures a statically trustworthy hypoglycemic effect on various types of mammals, including the human being, meaning it has a universal nature.

Moreover, doses required to reach the necessary therapeutic effect are comparable with the levels for injection insulin. But the said medicine possesses low resistant: properties, the term of experiment—up to 50 days as well as a comparatively low specific activity 20EA per 1 g of dry tablet.

The method for derivation of insulin-containing polymer hydro-gels, including immobilization of insulin in the volume of stitched polymer, modified by inhibitor of proteolitic ferments—ovomukoides (Ru Nr.2066551 Cl, 20.09.96).

The method enables to derive medicine, possessing activity, which makes 60–70% of the activity of insulin medicine during hypodermic injection. But the content of insulin in 1 g of hydro-gel is not high.

The closest to the invention proposed is the method for derivation of medicine for peroral use, including insulin incubation with erythrocytes in proportion 1–14:100 in the presence of stitching agent in final concentration 0.15–0.25% (Ru Nr.2058788 Cl, 20.04.96).

Consequently, medicine with the content 1000 E/1 g of dry mass has been derived with the storage period in lyophilized state—up to several years.

DISCLOSURE OF INVENTION

The task of the invention proposed is to create an insulin-containing medicine for peroral use, meaning resistant to the effect of proteolitic ferments in gastrointestinal tract with the increased insulin content in 1 g of dry substance, the fact that expands the potential for using the medicine in various medical forms.

The essence of the invention is as follows: insulin-containing medicine for peroral use represents insulin, immobilized on erythrocytes of fresh mammal blood in the presence of stitching agent in proportion %: insulin: erytces of fresh mammal blood 5–10:100 and auxiliary substance with the insulin content in lyophilized state 1250–2000 E of insulin per 1 g of dry mass.

The said medicine as an auxiliary substance may contain gelatin in the amount from 1 to 2,5%.

The said medicine includes erythrocytes excreted from the fresh pig, horse or human blood as erythrocytes during insulin immobilization The said medicine may contain glutarite dialdehyde as a stitching agent.

The method for derivation of insulin-containing medicine for peroral use includes the excretion of erythrocytes from fresh mammal blood, their incubation with insulin in proportion mass %: insulin: erythrocytes from fresh mammal blood 5–10:100 in final content of stitching agent 0,05–0, 35% within 4–6 hours under the temperature 4–8° C., along with this, in the process of excretion of erythrocytes the blood is influenced by centrifugal forces with the size 350–1100* g within 15–30 minutes, and when insulin is incubated with erythrocytes, pendular rocking of composition with the frequency 0.1–0.5 Hz occurs, moreover, washing of the immobilized insulin is performed in several cycles, given the effect of centrifugal forces in each cycle with the size 350–1100* g within 0.5–10 minutes.

The above stated immobilization conditions enable to increase insulin content in the immobilized product up to 1250–2000 E of insulin in 1 g of dry substance.

The technical outcome of the invention boils down to the fact that in maintaining stable hypoglycemic effect the activity and preservation qualities of the medical form derived is enhanced not only in a lyophilized but in a liquid state too.

The invention is implemented in the following way:

EXAMPLE 1

Erythrocytes were excreted from the fresh blood adding 1/10 volume of 3.8% sodium citrate during the effect of centrifugal forces 400* g within 30 minutes under the temperature 4° C. Erythrocytes were washed twice with four-fold volume 0.15M of sodium chloride solution. 20 ml of erythrocytes dredge were added by 10 ml of 0.1M of phosphate buffer solution pH 6.8 containing 0. 15M of sodium chloride, 50 ml of 1% crystal insulin solution and 1% of glutarite dialdehyde solution up to final concentration in the solution 0.05% and incubated the composition during pendular rocking with the frequency 0,5 Hz under the temperature 6° C. within 6 hours, proportion insulin: erythrocytes 5:100. Then the suspension was washed from the non-mixed up insulin and glutarite dialdehyde ten times with ten-fold volumes 0.15M of sodium chloride solution during the effect of centrifugal forces with the size 1100* g within 5 minutes. After the last washing the sediment was added by gelatin solution as a stabilizer up to final concentration 2.5%, stirred thoroughly for 10 minutes under the room temperature and dried in a lyophilized way.

Derived 2 g of ready product representing powder of brownish color with the content 1250 E of insulin on 1 g of dry product.

EXAMPLE 2

Derivation of insulin-containing medicine as in the example 1, except for the fact that 100 mg of 1% crysal insulin solution and afterwards glutarite dialdehyde was added up to final concentration 0.35% proportion insulin: erythrocytes 10:100. The composition was incubated for 4 hours. Prior to lyophilization gelatin was added up to final concentration 1%.

Derived ready product with insulin content 2000 E on 1 g of dry product. Proportion insulin: erythrocytess 10:100. Prior to use the medicine was emulged in the water up to required concentration.

EXAMPLE 3

Testing of insulin-containing medicine was conducted on rats with experimental diabetes, caused by streptozotocine. Streptozotocine was injected intraperitoneally into male rats as taken 120 mg/kg of animal mass. Streptozotocine was dissolved in citrate buffer pH 4,5 directly prior to injection. In 48 hours insulin-containing medicine, immobilized with the help of glutarite dialdehyde as taken 15–20 units of insulin in medicine (per one animal), prepared as in the example, was injected through probe into animals and in thee hours glucose content was determined in the animal blood. Animals with streptozotocine diabetes, which didn't receive insulin-containing medicine, served as control groups.

As seen from the figures in table 1, glucose level in the blood of animals with streptozotocine diabetes in three hours upon the injection of insulin-containing medicine reduced averagely by 65% in comparison with the diabetic animals, which didn't receive insulin-containing medicine.

EXAMPLE 4

Insulin-containing medicine, derived as in the example 1, was injected into adult male mice with mass 20 g through probe in the volume of 0,2 ml. The animals received 2,0–2,5 units of insulin in insulin-containing medicine. Glucose content in the blood was determined through glucose-oxide method The results are provided in table 2.

From the figures provided it is vividly seen that insulin-containing medicine when injected into mice reduces glucose level in the blood averagely by 55% in comparison with animals, which didn't receive insulin-containing medicine.

EXAMPLE 5

Insulin-containing medicine, derived as in the example 2 as taken 10–15 units, was injected into male rats with mass 150–180 g and in 3–6 hours glucose level was determined. Rats, which didn't receive insulin-containing medicine, served as control groups. The figures are provided in table 3.

As seen from the figures in table 3 those rats, which received insulin-containing medicine in 3 and 6 hours, showed reduction in glucose level in their blood, that made 52% and 53% respectively to the initial level, at a time when glucose level in the blood of control animals within the same time spell didn't change at all.

Medicine in the process of manufacturing or in a ready form may be processed by gelatin or any other inertial compound, and prior to use may be suspended in the water. Medicine may be manufactured in the form of tablets, protected by any inertial related, compound as well as applied in the form of suspension, which may be kept under the temperature +4° C. for not less than 3 months

TABLE 1

| Groups of animals | Quantity of animals | Glucose in blood, mM/l M ± m | p | % of reduction to control |
|---|---|---|---|---|
| Without insulin-containing medicine (norm, 100%) | 20 | 16.10 ± 0.74 | | |
| Insulin-containing medicine in accordance with the invention | 20 | 5.62 ± 0.44 | <0.01 | 65 |

TABLE 2

| Groups of animals | Quantity of animals | Glucose in blood, mM/l average | fluctuation limits | % of reduction to norm |
|---|---|---|---|---|
| Without insulin-containing medicine (norm, 100%) | 10 | 14.20 | 13.80 ± 4.22 | |
| Insulin-containing medicine in accordance with the invention | 10 | 6.21 | 5.74 ± 1.76 | 57 |

TABLE 3

| Groups of animals | Quantity of animals | Glucose in blood, mM/l initial | in 3 hours | % of reduction | in 6 hours | % of reduction |
|---|---|---|---|---|---|---|
| Insulin-containing medicine of peroral use | 10 | 15.5 ± 2.6< | 7.5 ± 2.4 p < 0.01 | 52 | 7.24 ± 1.78 p < 0.01 | 53 |
| Control without insulin-containing medicine | 10 | 15.6 ± 2.5 | 14.1 ± 2.5 p > 0.5 | 45 | 14.1 ± 2.6 p > 0.5 | 2.1 |

TABLE 4

| Duration of storage in years | Glucose content in blood** mM/l initial | in 3 hours | % of reduction |
|---|---|---|---|
| 0.01 | 15.5 ± 1.0 | 6.2 ± 0.5 | 60 |
| 0.5 | 14.8 ± 0.9 | 5.6 ± 0.4 | 62 |
| 1 | 16.1 ± 0.7 | 6.7 ± 0.6 | 58 |
| 2 | 15.0 ± 0.9 | 6.1 ± 0.5 | 59 |
| 4 | 16.5 ± 0.7 | 6.7 ± 0.7 | 61 |
| 5 | 14.9 ± 0.5 | 5.9 ± 0.6 | 6.0 |

*-dried in a lyophilized way
**-injection of medicine into rats with streptozotocine diabetes in peroral way Technical Applicability Insulin containing medicine for peroral use may be used not only for treatment of diabetes but for other types of pathology as well, followed by hyperglycemia (extensive surgical wounds, thermal injuries, septic condition, haemorrhoidal shock, anesthesia) as well as during pathological states characterized with the increased albumen decomposition and its decreased synthesis (various stages of burn disease, nephropathies etc.).

What is claimed is:

1. An insulin-containing medicine for peroral comprising an immobilized insulin, erythrocytes and a linking agent which links the insulin to the erythrocytes, in mass %:

| insulin | 5–10 |
|---|---|
| erythrocytes | 89.985–94.997 |
| linking agent | 0.003–0.015 | wherein the insulin-containing medicine is in a lypophilized form with a content of 1250–2000E of insulin per 1 g of dry mass.

2. The insulin-containing medicine of claim 1, further comprising an auxiliary substance.

3. The insulin-containing medicine of claim 1, wherein the auxiliary substance is gelatin.

4. The insulin-containing medicine of claim 1, wherein the amount of the auxiliary substance is 1–2.5 mass %.

5. The insulin-containing medicine of claim 1, wherein erythrocytes are excreted from fresh pig, livestock or horse blood.

6. The insulin-containing medicine of claim 1, wherein the erythrocytes are excreted from fresh human blood.

7. The insulin-containing medicine of claim 1, wherein the linking agent is glutarite dialdehyde.

8. The insulin-containing medicine of claim 1, wherein the insulin-containing medicine is derived by excreting erythrocytes from fresh mammal blood, incubating the erythrocytes with insulin in the presence of linking agent to obtain immobilized insulin, washing the immobilized insulin with a physiological solution to obtain an insulin solution, adding a stabilizer to the insulin solution, and lyophilizing the insulin solution, wherein the step of incubating is carried out at an insulin:erythrocytes ratio of 5–10:100 and with the content of linking agent in the final concentration 0.05–0.15 under the temperature 4–8° C. for 4–6 hours while pendular rocking the erythrocytes and insulin with a frequency of 0.1–0.5 Hz, wherein the step of excreting is influenced by centrifugal forces with a size of 350–1100 g within 15–30 minutes, and wherein the step of washing the immobilized is carried out in several cycles under centrifugal forces with a size of 350–1100 g within 0.5–10.0 per cycle.

9. The insulin-containing medicine of claim 8, wherein the stabilizer is gelatine.

10. The insulin-containing medicine of claim 8, wherein the stabilizer is gelatine in the quantity 1–2.5 mass %.

11. The insulin-containing medicine of claim 8, wherein the erythrocytes are excreted from fresh pig, livestock or horse blood.

12. The insulin-containing medicine of claim 8, wherein the erythrocytes are excreted from fresh human blood.

13. The insulin-containing medicine of claim 8, wherein the linking agent is glutarite dialdehyde.

\* \* \* \* \*